United States Patent
Blomberg et al.

(10) Patent No.: US 8,364,455 B2
(45) Date of Patent: Jan. 29, 2013

(54) SIMULATOR FOR USE WITH A BREATHING-ASSIST DEVICE

(75) Inventors: Urban Blomberg, Linköping (SE); Fredrik Jalde, Bromma (SE)

(73) Assignee: Maquet Critical Care AB, Solna (SE)

( * ) Notice: Subject to any disclaimer, the term of this patent is extended or adjusted under 35 U.S.C. 154(b) by 1336 days.

(21) Appl. No.: 11/915,472

(22) PCT Filed: Jun. 9, 2005

(86) PCT No.: PCT/EP2005/052674
§ 371 (c)(1), (2), (4) Date: Nov. 26, 2007

(87) PCT Pub. No.: WO2006/131150
PCT Pub. Date: Dec. 14, 2006

(65) Prior Publication Data
US 2008/0200966 A1    Aug. 21, 2008

(51) Int. Cl.
*G06G 7/60* (2006.01)
(52) U.S. Cl. .............. 703/11; 600/529; 607/42
(58) Field of Classification Search ........... 703/11; 128/204.21; 607/42; 600/529, 546
See application file for complete search history.

(56) References Cited

U.S. PATENT DOCUMENTS

| | | | |
|---|---|---|---|
| 5,300,096 A * | 4/1994 | Hall et al. | 607/48 |
| 6,200,331 B1 | 3/2001 | Swartz et al. | |
| 6,411,843 B1 * | 6/2002 | Zarychta | 600/546 |
| 6,980,863 B2 * | 12/2005 | van Venrooij et al. | 607/116 |
| 2003/0233049 A1 * | 12/2003 | Lampotang et al. | 600/500 |
| 2004/0068229 A1 * | 4/2004 | Jansen et al. | 604/154 |
| 2004/0110117 A1 | 6/2004 | Van Oostrom et al. | |
| 2005/0085865 A1 * | 4/2005 | Tehrani | 607/42 |
| 2005/0222643 A1 * | 10/2005 | Heruth et al. | 607/48 |
| 2006/0058852 A1 * | 3/2006 | Koh et al. | 607/42 |

FOREIGN PATENT DOCUMENTS

| | | |
|---|---|---|
| DE | 36 02 171 | 7/1987 |
| EP | 0 427 419 | 5/1991 |

OTHER PUBLICATIONS

Zoldac et al. "An electronic simulator for testing infant apnea monitors that utilizes realistic physiologic data." Case Western Reserve University. 1993.*
Hans Rudolph. "Series 1101 Breathing Simulator." 2001.*

* cited by examiner

*Primary Examiner* — Carl H Layno
*Assistant Examiner* — Eugene Wu
(74) *Attorney, Agent, or Firm* — Schiff Hardin LLP

(57) ABSTRACT

Function testing of a ventilator using an EMG or other bioelectric signal representative of the breathing of the patient to control ventilation is enabled by a simulating device for use with a breathing related device for monitoring and/or controlling a patient's breathing, the simulating device including a signal generator for providing a simulated bioelectric compound signal related to the patient's breathing function, and a contact for outputting the simulated bioelectric compound signal. The simulating device can also be used for training purposes and in the development of new ventilators.

12 Claims, 3 Drawing Sheets

SIMULATOR FOR USE WITH A BREATHING-ASSIST DEVICE

BACKGROUND OF THE INVENTION

1. Field of the Invention

The present invention concerns a simulator that is suitable for use with a breathing-assist apparatus that monitors and/or controls the breathing of a patient.

2. Description of the Prior Art

Ventilators are commonly used to provide assisted breathing to patients. The breathing support provided by a ventilator may be controlled in different ways to ensure appropriate ventilation of the patient. Traditionally the breathing support is based on measurements on the patient's ventilation, that is, air pressure and/or air flow in the patient's lungs, and the support is triggered by detection of the inspiratory efforts of the patient. The pressure or air flow must be measured continuously and it may be difficult to determine which part of the signal originates from the patient.

A breathing effort is controlled by the breathing centre in the brain, the main breathing muscle, the diaphragm, is activated through nerve transmission in the phrenic nerve. When the muscle is activated, it contracts and lowers the pressure in the thorax and thus creates an inspiratory flow.

A novel development in the field of ventilation improves the ventilator's responsiveness to the patient breathing efforts by sensing the inspiratory effort by detecting the electric activity, the electromyogram (EMG), of the contracting diaphragm. The electromyographic signal is picked up using an oesophageal array of electrodes. The signal is conditioned and a signal representative of the diaphragmal electrical activity, the EAdi, a is calculated. The supply of gas from the ventilator to the patient is then controlled in a suitable manner in proportion to the EAdi, in most cases the pressure delivered to the patient is controlled.

EP 1 205 202 discloses an EMG controlled ventilator system, but said system does not propose a way of ensuring that the units providing the EMG control of the ventilator actually work and provide correct signals.

Instead of EMG, another bioelectric signal indicative of the patient's breathing efforts may be used to control the ventilation. The new technology of EMG, or other bioelectric signal, controlled ventilation provides a powerful tool for physicians and medical personal working with patients in need of ventilation support, however it also causes new problems and challenges.

Apart from the new modes of ventilation, new equipment such as oesophageal probes or other sensors for detecting EMG or bioelectric signals representing respiratory activity is needed in to use the new technology.

The new requirements above calls for a solution to facilitate the work and improve the understanding for medical personnel and other professionals who use, produces, tests and develops ventilators controlled by EMG or bio-electric signals representing respiratory activity.

SUMMARY OF THE INVENTION

An object of the present invention is to facilitate function testing of a ventilator using an EMG or other bioelectric signal representative of the breathing of the patient to control ventilation.

The above object is achieved in accordance with the present invention by a simulating device for use with a breathing-assist device that monitors and/or controls breathing of a patient, the simulating device including a signal generator that provides a simulated bio-electric compound signal relating to the breathing function of the patient, and a contact arrangement that emits the bio-electric compound signal as an output.

The object also is achieved in accordance with the present invention by a method for operating a breathing-assist device that monitors and/or controls breathing by a patient, including the steps of providing a simulated bio-electrical signal related to the breathing of the patient, and feeding or supplying the simulated bio-electric signal to the breathing-assist device.

The simulating device according to the invention can be used to simulate a patient's interaction with the ventilator in system tests and function tests of the ventilator. The test may be controlled by a software program or may be operator controlled. The bioelectric signal may be an electromyographic (EMG) signal or another signal indicative of the breathing function, such as the signal generated in the phrenic nerve.

The simulating device according to the invention may also be used for other purposes. One important such purpose is training of medical personnel who are going to work with the ventilators. Breathing patterns and the effects of different support modes can be simulated as well as different patient conditions. The function and behaviour of the ventilator when different EMG characteristics are input can be simulated. If EMG recordings are used different typical cases, corresponding to real patients' conditions, may be emulated.

In one preferred embodiment the simulator is arranged to receive a feedback signal from the ventilator and adjust the simulated patient response in dependence of said feedback.

In this case, a change in the ventilation support will produce a change in the simulated EMG signal showing the effect of the applied therapy. In the same way a simulated change in the patient conditions, represented by a change in amplitude or frequency density/power spectrum, would change the response from the ventilator. An example of the interaction between a patient and a ventilator is described in the application entitled "Ventilator and method for controlling a ventilator", to be filed shortly by the same applicant. In particular the ventilator's response to changes in the patient's situation and vice versa is discussed.

In the above mentioned copending application the ventilation is controlled by amplifying the EMG signal (or other breathing related signal) using a gain factor. Two main embodiments are discussed: one in which the gain is varied so as to keep the ventilation pressure substantially constant and a second embodiment in which the gain is frozen at a suitable level. In the former case the support ventilation will be automatically adapted to the patient's needs. As the patient gets better the support ventilation will be gradually reduced so that it always matches the patient's needs. In the latter case, the physician is guaranteed to have control over the ventilation and a minimum ventilation is always ensured.

The simulating device can also be used for demonstrating the ventilator, for example, for marketing or sales purposes. It can also be used as a test tool in the development of new ventilators and software and catheters for ventilators.

To test the ventilator itself, different EMG patterns can be provided to the ventilator by the simulating device and the behaviour of the ventilator in response to these EMG patterns can be monitored to determine if the ventilator is functioning as it should. The simulating device can also be used for troubleshooting.

The signal generator may provide a bioelectric signal recorded from a human being as a simulated bioelectric signal. This embodiment may be particularly useful for training purposes.

For test applications of ventilators and catheters the simulated bioelectric signal may comprise a simulated EMG signal comprising a sine wave in a suitable frequency range. The suitable frequency range depends on the measuring equipment used. If an oesophageal catheter is used the frequency range depends in particular on the distance between the electrodes. The frequency range also depends on where on the patient the measurements are carried out, i.e. externally or internally. A theoretical background of the analysis of the EMG spectrum van be studied in "Power Spectrum Analysis of EMS Signals and Its applications" by Dr Lars Lindström et al, published in Computer-Aided Electromyography. How to measure the EMG spectrum for by means of oesophageal catheters, and how the spectrum is influenced by the positioning of the electrodes is discussed in "Influence of bipolar oesophagal electrode positioning on measurements of human crural diaphragm electromyogram" by Beck et al., 0161-7567/96 the American Physiological Society.

The patient EMG is a stochastic signal in the applicable frequency range as discussed above. Therefore, a more refined simulated signal would be a band pass filtered white noise signal according to the frequency ranges above.

Using a signal having well defined properties (frequency spectrum, amplitude) is advantageous in testing since it is easy to predict what the response on each channel should be. Thus, each channel can be tested separately in a reliable manner.

Instead of an EMG signal, the simulated bioelectric signal may comprise a simulated phrenic nerve signal. It would also be possible to use a combination of two different signals, for example monitoring the phrenic nerve signal and its effect on the EMG signal of the diaphragm.

The simulating device may include circuitry for varying the frequency of the simulated bioelectric signal.

The signal generator preferably provides a simulated bioelectric signal comprising a noise signal, including white noise, a simulated ECG signal and/or low frequency components such as motion artefacts and disturbance from the mains.

The simulating device preferably include circuitry for varying the amplitude of the simulated bioelectric signal and the amplitude of each component of the bioelectric signal relative to the other components.

Preferably the contact arrangement provides the simulated bioelectric signal on a number of channels corresponding to the channels recorded by the breathing assisting device when used on a human being. Different signals may be provided to each channel to simulate the signal detected by each electrode as when recording from a patient. The contact arrangement can be a hardware contact for connecting a simulating device according to the invention to a ventilator, or to a device simulating the function of a ventilator. The contact arrangement may also be software functions providing for communication between a simulating device according to the invention and a device simulating the function of a ventilator. For example, the inventive simulator and the ventilator simulator could both be software implemented in the same computer, in which case the contact arrangement would be implemented in software.

In one hardware embodiment the contact means arrangement is tubular and is provided with a number of electrical contacts on the inside so as to provide electrical contact to a catheter functioning as an input to the breathing assisting device.

This embodiment enables training of medical personnel in placement of the catheter. The effects of changing the position of the catheter can be studied.

This embodiment also makes it possible to test the catheter and its connection to the ventilator. The catheter can be connected to the simulating device and a test program may be run to ensure that all electrodes are working and that there are no short circuits or other defects.

As is common in the art the function of the simulator is controlled by computer program.

Thus the simulating device can be used together with a ventilator to provide an understanding of how the ventilator works in EMG mode including which parameters may be adjusted and how they affect the mode.

By integrating the simulating device of the invention with a test lung its use for training and education is broadened even more.

DESCRIPTION OF THE PREFERRED EMBODIMENTS

Figure 1:
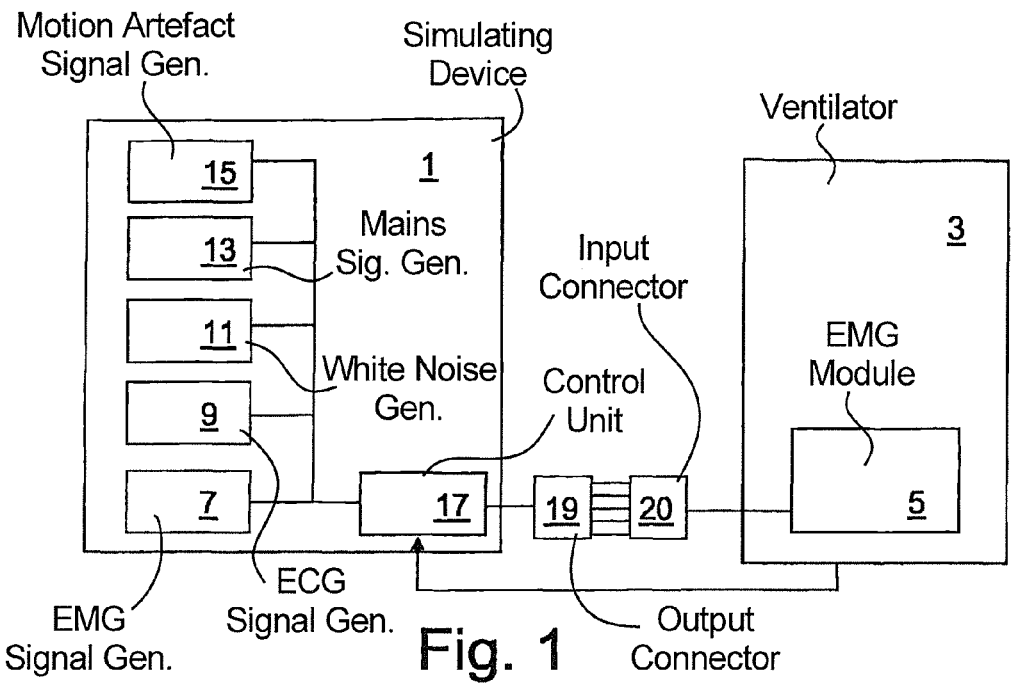
FIG. 1 illustrates a simulating device providing a signal to a ventilator according a first embodiment of the invention.

FIG. 1 illustrates a simulating device 1 according to a first embodiment of the invention. The simulating device 1 is connectable to a ventilator 3 for providing a simulated EMG signal to an EMG module 5 in the ventilator 3.

The simulating device 1 has an EMG signal generator 7 arranged to generate a simulated EMG signal. Instead of the EMG signal another signal indicating the patient's breathing may be used, such as the phrenic nerve signal of the patient. Preferably, the simulating device 1 also has an ECG signal generator 9 arranged to generate a simulated ECG signal that can be combined with the simulated EMG signal in order to simulate ECG interference which normally occurs in EMG signals.

The simulating device 1 may also has other signal generators 11, 13, 15 for simulating other disturbances to the EMG signal. Hence, the figure shows a white noise generator 11, to simulate the background noise, a mains signal generator 13 to simulate the 50 Hz or 60 Hz disturbances caused by the mains in the room, and a motion artefact signal generator 15 to simulate the low-frequency disturbances caused by the catheter movements in the patient and/or peristaltic movements in the patient.

The simulated EMG signal, with or without the simulated ECG signal, is fed, possibly through a control unit 17, to an output connector 19 arranged to be connected to an input connector 20 of the ventilator 3. The input connector 20 feeds the incoming simulated EMG signal to the EMG module 5 of the ventilator 3. The control unit 17, if present, controls the relative signal power of the signals provided by the signal generators 7, 9, 11, 13, 15.

The simulated EMS signal may be generated in a number of ways to provide a more or less good approximation of the EMG signal. A real patient EMG is a stochastic signal, the best simulation of which is a band pass filtered white noise signal in a suitable frequency range.

In its simplest form the simulated EMG signal may be a sine wave in the suitable frequency range. It can also embody several sine waves within the suitable frequency range. The suitable frequency range depends on a number of factors, as discussed above. A suitable frequency range is 100 Hz to 300 Hz or 70 Hz to 300 Hz, with its main power spectrum in the 100 Hz-150 Hz region.

The EMG signal generator 7 may be provided with means to vary the frequency to simulate the behaviour of different patients and/or different illnesses or states of sedation.

The simulated ECG signal may be a pulse signal emulating the normal ECG signal recorded from a patient, both as regards the frequency spectrum, amplitude and time between the pulses.

The simulated EMG signal and the other simulated signals may be combined in a passive junction. Preferably, however, all the simulated signals are fed to a control unit 17, which is able to adjust the signals relative to each other, for example with regard to the signal amplitudes, to produce a compound signal which will be the output signal from the simulating device 1. The control unit 17 may also be used to vary the amplitude of the combined signal. The control unit 17 also controls the activation and deactivation of the simulated signal. How often the simulated EMG signal is activated and for how long corresponds to the breathing frequency and the I/E ratio. Similarly, the simulated ECG signal can be activated at specific intervals and for specific durations corresponding to heart rate and PQRS duration.

The simulating device may also be provided with a pushbutton or other manually operable switch for activating/deactivating the compound signal. For the ECG signal a mechanical switch is not recommended since the ECG should normally be connected for about 100 ms.

As indicated by the output connector 19 the simulating device 1 is preferably arranged to provide a plurality of simulated compound signals, corresponding to the input channels to the ventilator 3.

The simulator may be arranged to respond to a feedback signal from the ventilator 3, preferably provided to the control unit 17. The feedback signal indicates the ventilation support, or change in ventilation support, which may be caused by the signals provided from the simulator to the ventilator, or because of changed settings of the ventilator (for example, the gain). The feedback signal in turn causes a simulated change in the patient's condition, which may affect the intensity, frequency density and/or power spectrum of the simulated compound signal. The changes in the simulated signal are controlled by software arranged to interpret the feedback signal in terms of the effect it would have on a real patient and adjust the compound signal accordingly.

One simple way of responding to the feedback signal would be to adjust the amplitude of the EMG signal. This can be done both if the simulated compound signal is a synthetic signal and if it is a recorded EMG signal. As an alternative a data base of signals recorded from patients and representing different types of conditions could be used. The data base could also include synthetic signals corresponding to parameter changes, pathological conditions, disturbances (such as motion artefacts) etc., where a lookup table could be used to select the appropriate signal response to the feedback from the ventilator. In a similar manner the ventilator's response if the patient's parameters are changed can be seen.

Instead of providing the feedback signal to the control unit 17 it could be provided to one or more of the signal generators 7, 9, 11, 13, 15, to affect the amplitude and frequency spectrum of the signal generated in the generator concerned.

Figure 2:
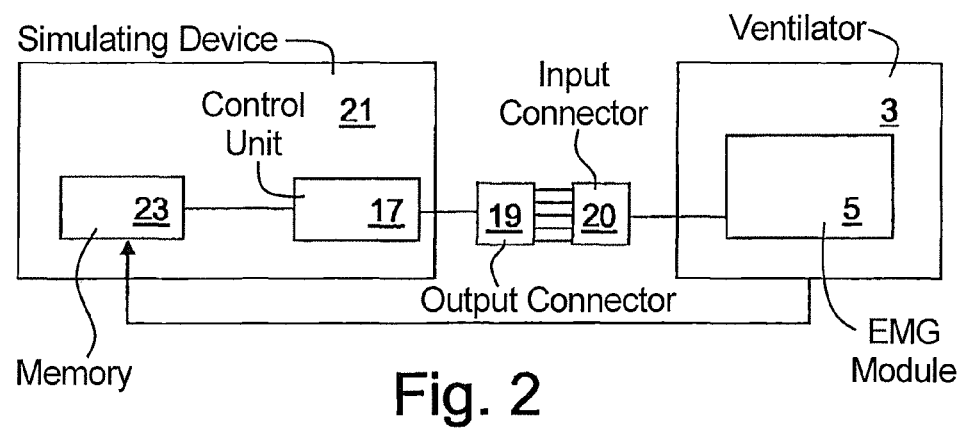
FIG. 2 illustrates a simulating device according a second embodiment of the invention.

FIG. 2 illustrates a simulating device 21 according to a second embodiment of the invention. As before, a ventilator 3 has an EMG module 5 arranged to receive an EMG signal through an input connector 20. Instead of the signal generator 7 in FIG. 1, the simulated EMG signal in this embodiment is an EMG signal recorded from an actual patient and stored in a memory 23. This EMG signal will already comprise the disturbances normally found in an EMG signal, such as an ECG signal and other signals mentioned above. Therefore, there is no need for a separate ECG signal generator. The simulated compound EMG signal is provided to the output connector 19, preferably through a control unit 17 arranged to control the amplitude of the signal.

The simulator 21 shown in FIG. 2 can also be arranged to receive a feedback signal from the ventilator, in a similar way to the simulator 1 of FIG. 1. In this case the feedback signal can be provided to the control unit 17

Of course, the two embodiments shown in FIGS. 1 and 2 can be combined, so that a simulating device comprises both signal generators 7, 9, 11, 13, 15, and a memory 23. In this way the simulating device will have the possibility of providing a generated EMG signal, with or without disturbances, having the desired characteristics, or an actual recorded EMG signal. Disturbances can also be added to the recorded EMG signal, for example, to test the effects of mains disturbance.

The simulator according to FIG. 1 or 2 can be implemented as an autonomous hardware implemented embedded processor assembly. It can also be computer program run on a computer, such as a personal computer comprising a D/A card for converting digital signals to analogue signals.

Of course, instead of actual recorded EMG signals the memory 23 may comprise one or more generated signals arranged to emulate EMG signals.

One simple way of responding to the feedback signal would be to adjust the amplitude of the EMG signal. This can be done both if the simulated signal is a synthetic signal and if it is a recorded EMG signal. As an alternative a data base of signals recorded from patients and representing different types of conditions could be used. The data base could also comprise synthetic signals corresponding to parameter changes, pathological conditions, disturbances (such as motion artefacts) etc., where a lookup table could be used to select the appropriate signal response to the feedback from the ventilator. In a similar manner the ventilator's response if the patient's parameters are changed can be seen.

In all the embodiments above, the input connector 20 of the ventilator is preferably the input connector used for connecting the catheter to the ventilator to provide EMG signals to the EMG module when the ventilator is used with a patient. In this case, the output connector 19 of the simulating device should be designed in such a way that it matches the input connector 20. These connectors can be designed in different ways depending on the type of ventilator. The skilled person will be able to design a connector for a particular ventilator.

Figure 3:
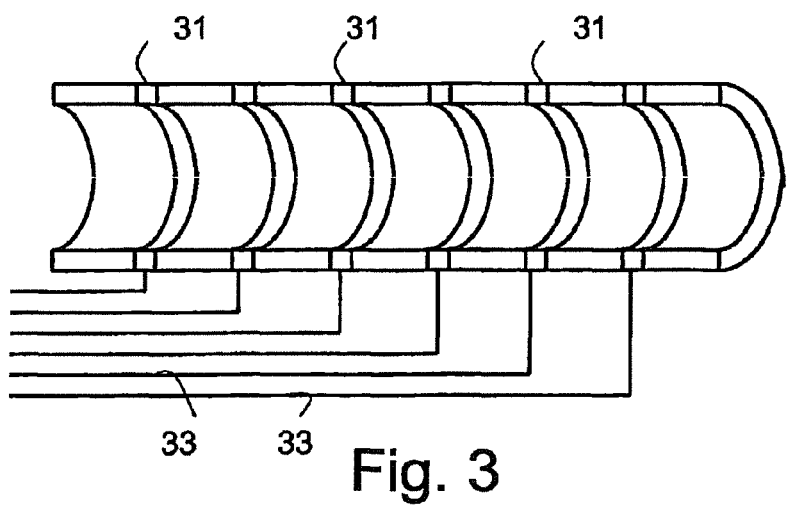
FIG. 3 illustrates schematically one embodiment of a connection between the simulating device and a catheter connected to a ventilator.

Alternatively the catheter can be used for connection, in which case the output connector 19 of the simulator must match the design of the catheter. A cross-sectional view of one such output connector is shown in FIG. 3. Typically, the catheter is shaped as a string having electrodes arranged at regular intervals. In this case the output connector 19 could be shaped as a tube, for example a silicone tube having electric contacts 31 on the inside of the tube at regular intervals matching the positions of the electrodes on the catheter. In FIG. 3 six contacts 31 are shown. The electric contacts are individually connectable to the simulator through electrical connectors 33 for receiving individual EMG signals. To connect the ventilator to the simulator in this case the catheter can be inserted into the tubular output connector. In this embodiment the catheter itself and its connection to the ventilator can also be tested.

Preferably, in all embodiments, the channels are individually connectable, to enable testing of each channel individually, and different signals can be applied on different channels, so as to simulate a real situation in which the electrodes will record different signals depending on their position relative to the diaphragm and other organs of the patient.

Instead of connecting the simulating device 1 to a real ventilator 3, a simulated ventilator can be used. The simulated ventilator can be software implemented in the same processing unit as is used for the inventive simulating device 1. In this case no hardware connection may be necessary. Instead, parameter values may be exchanged between software modules of the two simulating devices.

Figure 4:
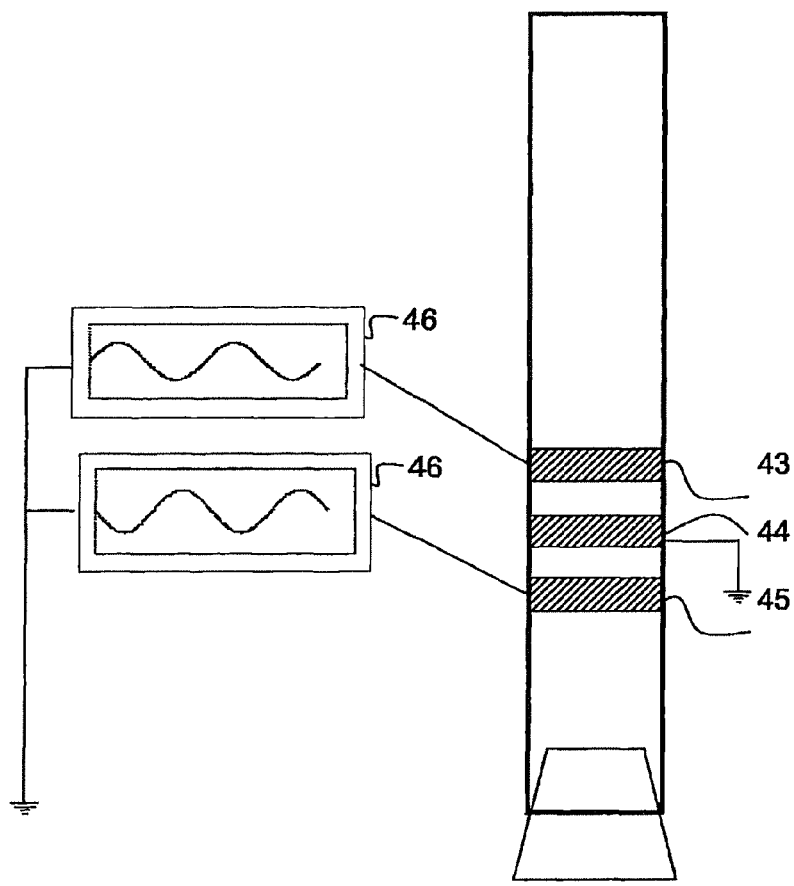
FIG. 4 illustrates a first embodiment for testing the function of a catheter, for which a simulating device according to the invention may be used.
Figure 5:
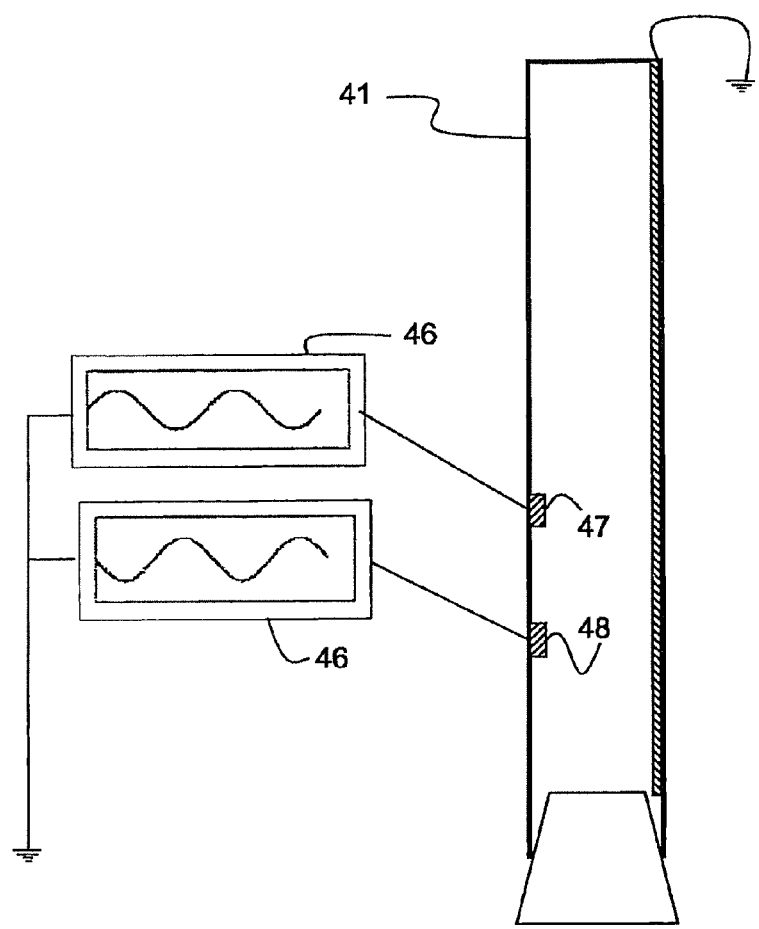
FIG. 5 illustrates a second different embodiment for testing the function of a catheter, for which a simulating device according to the invention may be used.

FIGS. 4 and 5 illustrate two different embodiments for testing the function of a catheter, for which a simulating device according to the invention may be used. In each of these embodiments a plastic tube 41 filled with water is used to apply signals to at least some of the electrodes of the catheter. The voltage signals applied to the electrodes In FIG. 4, metal foil electrodes 43, 44, 45 are placed around the outside of the tube. FIG. 4 shows three electrodes placed at equal distance from each other to apply signals to three of the catheter's electrodes (not shown). Simulated signals from the simulator described above are applied to two of the electrodes 43, 45. In FIG. 4, the middle electrode 44 is connected to ground, to increase the electric field in the water. This simulates the situation when the catheter is inserted in a patient's oesophagus, with the middle electrode 44 close to the diaphragm and the two other electrodes are placed at the same distance from the diaphragm but on different sides. In FIG. 4, three signal generators 46 are shown, each arranged to provide a signal to one of the electrodes.

If the catheter is positioned correctly the output signal will be maximized if the input signals at the two electrodes 43, 45 have opposite phases and minimized when they have the same phase. By moving the catheter in the tube the sensitivity and positioning of the different catheter electrodes can be evaluated.

In FIG. 5 electrodes are mounted inside the plastic tube 41. In this case two electrodes 47, 48 are shown, which do not extend around the tube 41. The voltage sources 46 that generate the simulated signals are connected to the same ground as the reference electrode of the catheter (not shown). If the catheter electrodes are not circular this configuration enables the detection of direction sensitivity in the catheter. In this case the catheter should be mounted in such a way that it is stretched and kept in the centre of the tube. When the catheter is rotated any directional sensitivity of the catheter can be observed.

As previously mentioned, there are a number of potential uses for the novel device such as demonstrating, training, education, research and testing. For all these applications the standard set-up comprise a ventilator, a test lung, catheters of various types and a simulator with catheter docking means. The set-up could of course be substituted, partly or as a whole, by a computer.

An example of training and education is to teach the operator/student on how to place the catheter. If the catheter not is inserted far enough in the oesophagus the EMG signal will be drenched in ECG, and if it inserted too far the recorded EMGdi will be weak and drenched in noise. It is also possible to study the effects of motion artefacts, from file or simulation by hand.

Furthermore, an obvious but important feature is to train the operator/student of how to use the novel technology with its new breathing modes, the behaviour of the ventilator and how to interpret the EMG signal under normal conditions. This is important since the next step is the study of pathological recordings or simulations. In fact, the physician can be helped to diagnose the patient by the machine by interpreting the EMG and breathing patterns.

The test lung and the feedback system will make it possible to study the effect of an applied therapy, or catheter placement, and all this can be made without putting a real patient at risk. The examples above are also suitable for demonstration and marketing.

Regarding research and testing it will be possible to use the simulator when developing new ventilation modes, catheters. This device opens up the possibility to test new software and make a first evaluation without animal tests in the first place, and the robustness of algorithms regarding various noise signals can be evaluated. Hardware, such as catheters, can be tested in the same manner.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method of operating an assembly of a breathing-assist device and a simulating device comprising the steps of:
   in said simulation device, generating a simulated bioelectrical signal related to breathing by a respiratory subject;
   supplying said simulated bioelectrical signal from the simulation device to the breathing-assist device;
   controlling operation of the breathing-assist device to produce breathing assistance, which otherwise occurs in response to an actual bioelectrical signal obtained from a patient, dependent on the simulated bioelectrical signal related to breathing by a respiratory subject, in a same manner as occurs in dependence of said actual bioelectrical signal and generating a feedback signal in said breathing-assist device that is indicative of said breathing assistance; and
   providing said feedback signal from the breathing-assist device to the simulation device and, in the simulation device, adjusting the simulated signal in response to the feedback signal.

2. A method according to claim 1, comprising providing the simulated bioelectric signal as a noise signal.

3. A method according to claim 2, comprising providing the noise signal as white noise.

4. A method according to claim 2 comprising providing the noise signal comprises a simulated ECG signal.

5. A method according to claim 1, comprising providing a bioelectric signal recorded from a human being as a simulated bioelectric signal.

6. A method according to claim 1, comprising providing the simulated bioelectrical signal as at least one sine wave in a frequency range between 70 Hz and 300 Hz.

7. A method according to claim 1, comprising providing the simulated bioelectric signal as a simulated phrenic nerve signal.

8. A method according to claim 1, comprising varying a frequency of the simulated bioelectric signal.

9. A method according to claim 1, comprising varying an amplitude of the simulated bioelectric signal.

10. A method according to claim 1, comprising providing said simulated bioelectric signal on a plurality of channels corresponding to channels recorded by the breathing-assist device when used on a human being.

11. An assembly comprising:
- a simulating device connected to a breathing-assist device for monitoring and/or controlling a patient's breathing,
- said simulating device comprising a signal generator that provides a simulated bioelectric compound signal related to the patient's breathing function;
- a contact arrangement that emits said simulated bioelectric compound signal as an output in a form serving as a control signal to the breathing-assist device;
- said breathing-assist device comprising a control unit configured to operate the breathing-assist device in response to an actual bioelectric compound signal obtained from a respiration subject to monitor and/or control breathing, and said control unit having an input that receives the control signal and said control unit being configured to operate the breathing-assist device dependent on the control signal in a same manner of operation as a response to said actual bioelectric compound signal; and
- a feedback circuit that registers a feedback signal indicative of the breathing support provided by the breathing-assist device and responsive circuitry configured to adapt the simulated signal in response to the feedback signal.

12. A non-transitory computer-readable storage medium encoded with a data structure loadable into a computerized simulation device, said data structure causing said simulation device to:
- generate a simulated bio-electric compound signal relating to a breathing function of a respiratory subject;
- emit said simulated bio-electric compound signal as an output in a form that operates a breathing-assist device to provide breathing assistance in a same manner as when the breathing-assist device is operated in response to an actual bioelectric compound signal obtained from a patient; and
- receive a feedback signal from the breathing-assist device indicative of said breathing assistance and adjust the simulated signal in response to the feedback signal.

* * * * *